United States Patent [19]

Bernstein et al.

[11] 4,024,403

[45] May 17, 1977

[54] X-RAY CARDIOVASCULAR EXAMINATION APPARATUS

[75] Inventors: Stanley Bernstein, Whitefish Bay; Philip J. Griswa, Waukesha; Paul Halter, Jr., Brookfield; Harold J. Kidd, Waukesha, all of Wis.

[73] Assignee: General Electric Company, Schenectady, N.Y.

[22] Filed: Mar. 19, 1976

[21] Appl. No.: 668,618

[52] U.S. Cl. .............................. 250/445 R; 250/446
[51] Int. Cl.[2] .................. A61B 6/04; G01N 21/34; G01N 23/04; G21K 5/06
[58] Field of Search ............ 250/446, 445 R, 445 T

[56] References Cited
UNITED STATES PATENTS 2,823,316  2/1958  Reynolds ..................... 250/445 R
3,281,598  10/1966  Hollstein ..................... 250/445 R

*Primary Examiner*—Alfred E. Smith
*Assistant Examiner*—T. N. Grigsby
*Attorney, Agent, or Firm*—Ralph G. Hohenfeldt

[57] ABSTRACT

An X-ray source is mounted in an enclosure for angulating longitudinally about a horizontal axis. An X-ray permeable patient supporting table is mounted on the top of the enclosure for executing lateral and longitudinal movements. An X-ray image receiving device such as an X-ray image intensifier is mounted above the table on a vertically movable arm which is on a longitudinally movable carriage. Electric control means are provided for angulating the X-ray source and image intensifier synchronously as the image intensifier system is shifted longitudinally or vertically such that the central ray from the X-ray source is kept perpendicular to the image input plane of the image intensifier.

23 Claims, 6 Drawing Figures

X-RAY CARDIOVASCULAR EXAMINATION APPARATUS

BACKGROUND OF THE INVENTION

This invention relates to X-ray cardiosvascular examination apparatus which can be used for general purpose X-ray examinations also.

An established procedure for examining the vascular system of organs such as the heart involves injecting a radiopaque dye into the blood vessels and fluoroscoping the organ of interest with a suitable X-ray image to optical image converting device such as an X-ray image intensifier. The dye outlines the heart and the associated vascular system which can then be observed while it is functioning for circulatory obstructions, aneurisms and other defects. As is well known, in an intensifier, the X-ray image impinges on a fluorescent screen which is the image input plane of the intensifier. The fluorescent image is converted into an electron image and then into a miniaturized bright optical image which may be viewed with a video camera or recorded with a cine camera or a spot film camera. The fluoroscopic image from the intensifier as viewed by the video camera is displayed on a video monitor. One of the problems with this procedure is that certain important blood vessels are often disposed with their axes perpendicular to the viewing plane, thus making defects difficult to observe. In other instances, blood vessels in the heart are superimposed or concealed by other vessels so it is difficult to distinguish them and to observe the defects in them.

Angulating the image intensifier and X-ray source jointly is one approach to viewing blood vessels in the heart perpendicular to the viewing plane rather than axially. Angulation also permits viewing between vessels that would otherwise be superimposed or obscured if they were other than parallel to the viewing plane.

Some prior apparatus for performing the specialized vascular procedures have an X-ray source arranged on one side of the patient and an image intensifier system on the other side with the source and system on a common mounting which causes the central X-ray beam to remain directed at the image plane for various angles at which viewing of the heart or blood vessels is desired. In some prior apparatus, the patient is supported for limited lengthwise turning and longitudinal angulation relative to the X-ray beam to provide for viewing the heart at various angles. In other designs, the X-ray source can be angulated longitudinally while the patient is supported for limited lengthwise rotation or no rotation at all.

Typically, in X-ray apparatus used heretofore for the purposes indicated, the X-ray source and imaging devices are supported on the ends of a U-shaped or a C-shaped arm which can approach the patient endwise or laterally. Angulation is achieved by rotating the C-arm about a laterally extending axis or the U-arm about a longitudinal axis and angulating the source and intensifier longitudinally. The problem with either of these designs is that the patient is supported on a table and the source and intensifier are in free space. A major disadvantage of this open construction is that shielding the operator from stray and secondary X-radiation is difficult, if not impossible.

SUMMARY OF THE INVENTION

In accordance with the invention, an X-ray source is mounted on one side of a patient supporting table for being motor driven angularly and an X-ray image intensifier system is mounted on the other side of the table for being shifted longitudinally and vertically to the position where angulation is desired. Motor means are provided for driving the intensifier angularly, synchronously and coordinately with the X-ray source such that the central X-ray beam from the source is maintained in perpendicularity at all times with the X-ray image input plane of the image intensifier. The X-ray source is preferably within a table structure or enclosure. A servo motor is coupled with the source for driving it angularly about a transverse or laterally extending axis. The X-ray image intensifier is mounted on a vertically movable and horizontally translatable means above the table. The intensifier also has a servo motor for driving it angularly about a laterally extending axis synchronously with the X-ray source. In a preferred embodiment, means are also provided for driving the X-ray source and patient supporting table up and down selectively to improve angular viewing even more.

In accordance with the invention, coordination of angles and positions of the apparatus components is made automatic by providing means for developing electric error signals which are functionally related to the position or angulation of the various components of the apparatus. The signal developing means are typified by potentiometers which are connected in a bridge circuit such that if any component position or angle changes, all the others will change coordinately. This keeps the central X-ray beam from the source always perpendicular to the image input plane of the image intensifier.

An advantage of the new apparatus is that there is no mechanical connection between the image intensifier system on one side of the X-ray table and the X-ray source on the other side of the table. In a practical sense, this means that there is no link arm between the image receiving intensifier and the X-ray source which would interfere with the examiner working on the patient supported on the table. The absence of interfering objects is important when emergency procedures involving several assistants must be resorted to during an examination.

An object of the invention is to provide an electrical control system which coordinates angulation of the X-ray source and an X-ray image receiving means such as an image intensifier or other fluoroscopic or image recording device automatically.

Another object is to provide separate but coordinately functioning motor drives for angulating the X-ray source and the image receiving means.

A more specific object is to provide a simple but effective angulation control system for X-ray cardiovascular examination apparatus.

How the foregoing and other more specific objects of the invention are achieved will appear in the course of the ensuing more detailed description of a preferred embodiment of the invention which will now be set forth in reference to the drawing.

DESCRIPTION OF THE PREFERRED EMBODIMENT

Figure 1:
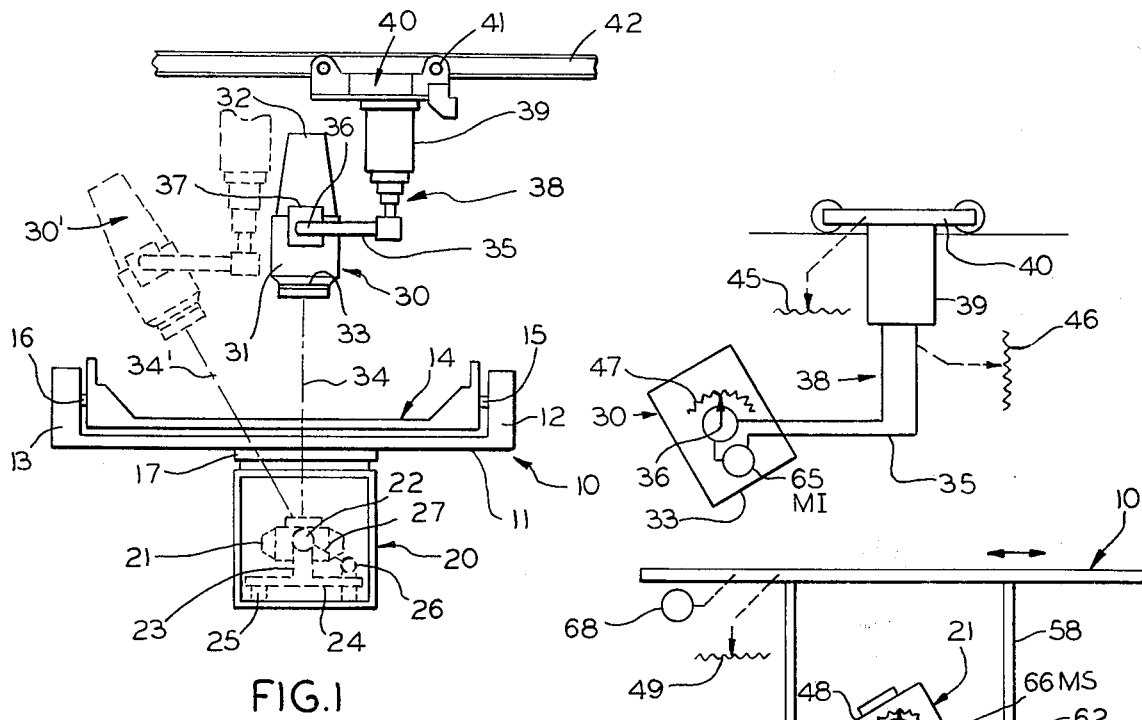
FIG. 1 shows a front elevation view of an X-ray apparatus in which the new motor angulated X-ray source and X-ray image intensifier and the new control system therefor may be employed.

The apparatus in FIG. 1 comprises an X-ray table assembly which is generally designated by the reference numeral 10. The table has a flat base 11 with upstanding ends 12 and 13. A cradle in which the patient is supported during an examination is marked 14. The cradle is mounted on power driven shafts 15 and 16 so that the cradle and patient thereon may be rotated through a substantial angle in either direction about a longitudinal axis. Table base 11 is supported on an enclosed structure 17 which has the necessary internal clearances for permitting an X-ray beam to be projected upwardly through a patient on cradle 14. Within enclosure 17 are suitable components, not visible, for enabling table base 11 to be shifted laterally, that is, in either direction perpendicular to the plane of the drawing. There are also components, not shown, for permitting the table base 11 to be shifted in opposite longitudinal directions, that is, in parallelism with the plane of the drawing. The mechanism for shifting the table longitudinally and laterally is known and need not be described.

Enclosure 17 is supported on housing 20, which except for a part of its top, is X-ray impermeable. Within housing 20 is an X-ray tube casing 21 in which there is a conventional X-ray tube, or source as it is referred to herein, not visible. Casing 21 is mounted for being angulated about a horizontal laterally extending axis 22 that is preferably substantially coincident with the focal spot on the X-ray tube target. X-ray tube casing 21 is supported for angulating on a stand 23 which has a base 24. The stand and base are schematically represented. The base is movable vertically with respect to schematically represented stationary members 25. In one embodiment of the invention, as will be discussed later, the X-ray tube casing 21 and the table assembly 10 are adapted for being elevated and lowered jointly. X-ray tube casing 21 is subject to longitudinal angulation about lateral axis 22 by operation of a reversible servo motor 26. The mechanical drive between motor 26 and casing 21 is symbolized by the dashed line 27.

Located above table assembly 10 is an image receiving means such as the X-ray image intensifier assembly which is indicated generally by the reference number 30. Intensifier assembly 30 comprises a lower housing portion 31 in which there is a conventional X-ray image intensifier tube, not visible. The upper part of assembly 30 has another housing portion 32 in which a video camera, not visible, is located. Although spot film and cine cameras are not illustrated as being mounted on upper housing 32, it will be understood by those skilled in the art that these components are usually present in X-ray image intensifier or fluoroscopic systems for vascular examinations. For the sake of illustration, one may consider that the input plane of the intensifier on which the X-ray image impinges is at the level of a line 33 which is coincident with the plane. The central ray from X-ray source 21 is suggested by the dash-dot line 34. Effective use of the apparatus requires that central X-ray 34 remain perpendicular to image plane 33 at all times. The improvements to be discussed in detail hereinafter facilitate maintaining perpendicularity between the central ray 34 of the X-ray beam and image plane 33.

Image intensifier assembly 30 is on longitudinally and vertically movable mounting means. Thus, the intensifier assembly is mounted on an arm 35 for pivoting about a laterally directed axis 36 through limited opposite longitudinal angles. Typically, intensifier 30 can be angulated longitudinally 35° caudally and 15° cranially. The caudal and cranial terms are based upon the assumption that the patient's head will be at the end of the table that has shaft 15 and the feet will be at the end that has shaft 16.

Image intensifier assembly 30 is subject to being angulated on arm 35 about lateral axis 36 under the influence of a servo motor, not visible in FIG. 1, which motor is within a housing 37.

Arm 35 is attached to one of a group of vertically extensible and contractible telescoping members 38 which are counterpoised in any of several known ways and are movable within themselves and in respect to a vertically immovable base 39. The base is suspended from a carriage 40 which has wheels such as 41 that permit the carriage to translate longitudinally and parallel with the X-ray table 11 on a rail system 42. Thus, it will be evident that image intensifier assembly 30 is vertically movable on telescoping members 38 and that it is subject to longitudinal translation on carriage 40 and subject to angulation about axis 36. Due to the new automatic control system which will be described in detail hereafter, when carriage 40 is shifted longitudinally, the X-ray image intensifier assembly 30 is angulated and the X-ray tube casing 21 is angulated synchronously so that the central X-ray 34 of the X-ray beam will maintain perpendicularity with the image plane 33 of the intensifier. This means that the image plane can be maintained in parallelism with the plane of interest in the patient's anatomy. Caudal translation and angulation of the image intensifier is suggested by the phantom view of the image intensifier which is marked 30'. It will be understood that, in respect to FIG. 1, when the image intensifier 30 is shifted longitudinally and automatically angulated, the X-ray source 21 will angulate synchronously and the central beam 34' will remain perpendicular to the image plane.

Figure 2:
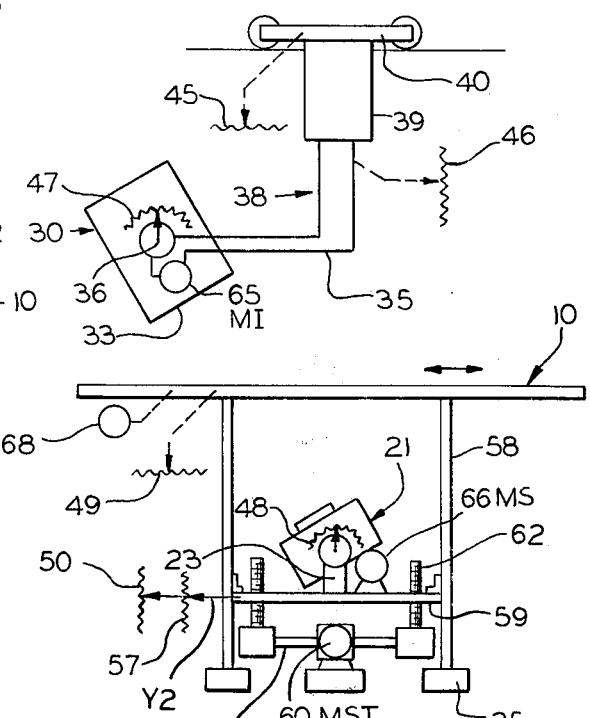
FIG. 2 is a more schematic view of the type of apparatus shown in FIG. 1 except that in this Figure the mechanical components are shown schematically to better illustrate the relationship with associated analog voltage developing potentiometers which are used in the illustrative control system.

The improvements which enable synchronous and coordinated control of the X-ray image intensifier 30 and X-ray tube casing 21 will now be described in detail in reference to FIGS. 2–4. In FIG. 2, several position sensors consisting of resistance potentiometers are mounted to sense longitudinal position of carriage 40, intensifier height 39, intensifier angle and X-ray tube casing 21 angle. There are also potentiometers for sensing longitudinal position of the X-ray table assembly 10 and the height of the table.

In FIG. 2, longitudinal position of carriage 40 is sensed by a schematically represented potentiometer 45. Potentiometer 45 produces an analog voltage signal which corresponds with or is a function of distance (XI) through which carriage 40 and, hence, image intensifier 30 is moved in the X direction. Another potentiometer 46 produces a signal which is a function of the height of the laterally directed angulation axis 36 and hence the height (YI) of intensifier 30. A potentiometer 47, mounted on image intensifier 30 produces a signal which is a function of $\theta$, the intensifier angle, or tan $\theta$ the tangent function thereof. X-ray tube casing 21 has a potentiometer 48 which produces a signal which is a function of the angle ($\theta S$) or its tan $\theta$, of the X-ray tube casing 21. A potentiometer 49 produces a voltage that is a function of the table longitudinal position (XT). Two potentiometers 50 and 57 produce a voltage or voltages which are a function of the height (Y2) of X-ray table 10 in conjunction with X-ray tube casing 21. The table height is sometimes adjusted to facilitate transferring a patient from a hospital cart or stretcher. It is also adjusted to provide a convenient work height for the examiner.

In FIG. 2, the X-ray table 10 is shown mounted on a schematically represented frame 58 which is on stationary members 25. In the actual embodiment the frame would be in an X-ray shielding enclosure as in FIG. 1. X-ray tube casing 21 and the stand 23 on which it angulates are mounted on a base, symbolized by a platform 59 that is fastened to frame 58. A motor 60, also marked MST for indicating that it moves the source and table, has laterally extending shafts such as 61 which drive one or more lead screws 62. The lead screws are threaded into plate 59 in this symbolic representation so that their rotation in one direction will raise table 10 and in the other direction will lower table 10. This function permits controlling the distance between the focal spot of the X-ray tube and the input image plane of the intensifier.

First motor means comprising a servo motor for driving X-ray tube casing 21 angularly is marked 66 and MS to imply that it turns the source on its axis. Second motor means comprising a servo motor for driving image intensifier 30 angularly is marked 65 and MI in FIG. 2. The third motor means comprising the servo motor for translating the X-ray table longitudinally is marked 68 and MT. The fourth motor means comprising the motor for adjusting the elevation of the X-ray source and table jointly is marked 60 and MST.

Figure 3:
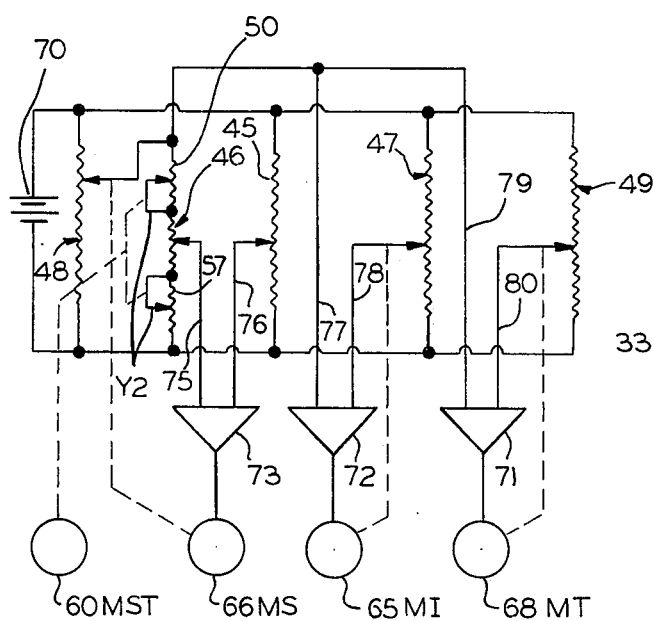
FIG. 3 is a circuit diagram of the control system.

The various potentiometers and motors shown in FIG. 2 are connected in a bridge circuit which is shown in FIG. 3. Besides the interconnecting wires shown in this Figure, the only elements which have not as yet been mentioned are a dc power source 70 and servo amplifier 71, 72 and 73. These are conventional null comparator amplifiers. When there is a difference or error signal between their inputs, they drive their associated motors 68, 65 and 66, respectively, until the error signal is nullified.

The structure and function of the FIG. 3 circuit will now be described concurrently. Assume that the image intensifier 30 is positioned initially with its axis of angulation 36 vertically above the X-ray source axis of angulation 22 and that the intensifier is then shifed by the operator or examiner longitudinally from its solid line position in FIG. 1 through the distance XI in FIG. 4 at which the intensifier will be angulated to obtain the desired view. In the initial centered position, of course, the central ray 34 from the X-ray tube is vertical and perpendicular to the image input plane 33 of intensifier 30. The intensifier would usually be shifted longitudinally to take a view perpendicular to the plane in the patient's anatomy that is not perpendicular when the intensifier is vertical. To achieve this result, the intensifier must be shifted and angulated so the central X-ray 34 will be perpendicular to the new angular plane in the anatomy and to the input image plane 33 of the intensifier.

Figure 4:
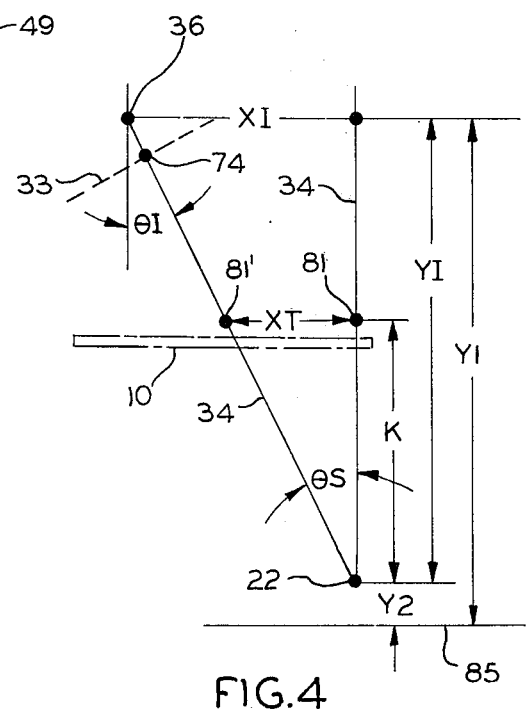
FIG. 4 is a diagram which is useful in explaining results obtainable with the control system.

In reference to FIG. 4, if the rotational axis 36 of the intensifier has been shifted through the distance XI the central X-ray 34 will then describe the angle $\theta S$ in respect to the rotational axis 22 of the X-ray tube. The center point 74 of image input plane 33 of the intensifier will shift to the positions shown and it will be necessary to incline plane 33 such that the angle $\theta I$ is obtained. $\theta I$, the angle of the intensifier, will then equal $\theta S$, the angle of the source.

In FIG. 3, the error signal produced by shifting the intensifier through a distance XI changes the signal level to one input 76 of comparator servo amplifier means 73 because the slide arm on potentiometer moves in correspondence with longitudinal movements of the intensifier. This signal unbalance causes motor 66 or MS to be driven such as to angulate the X-ray tube casing or source 21 through the angle $\theta S$. Motor MS will simultaneously drive the arm having a potential corresponding with tan $\theta S$ on potentiometer 48, thus changing its output potential. This new potential is applied to input 77 of comparator servo amplifier means 72 which causes motor MI to drive the intensifier 30 through the angle $\theta I$. At the same time, motor MI drives the arm having a potential corresponding with tan $\theta I$ on potentiometer 47. When $\theta I$ is attained, the input to amplifier 72 is nulled and motor MI stops and the intensifier stops turning. Now angles $\theta S$ and $\theta I$ and their tangents are equal. Central X-ray beam 34 will be perpendicular to image plane 33 of the intensifier.

Note that the resistance of potentiometer 48 is connected directly across regulated voltage source 70. The potential on the arm or sliding contact of potentiometer 48 corresponds with tan $\theta S$, where $\theta S$ is the angle of the X-ray source. When the arm is at the lowermost end of the resistance, the tan $\theta S$ potential is zero. Zero condition exists when the X-ray source and intensifier rotational axes are vertically aligned and if the intensifier is not shifted yet, its potential would also be zero and the potentiometer arm XI which is connected to amplifier input 76 and has the signal which is a function of would be at the lowermost end of the resistance of potentiometer 45.

The arm of potentiometer 46 has a potential on it which is a function of the height (YI) of the intensifier axis 36 relative to the X-ray source axis of angulation 22. This potential is multiplied by the potential on the arm of potentiometer 48 which is corresponds with tan $\theta S$ since the potential on the arm of potentiometer 48 is applied to the top of the resistance of potentiometer 46. By way of example, if the source 70 voltage were one volt and the arm or sliding contact were at the top of potentiometer resistance 48, one volt would appear on the arm as representing a particular angle $\theta$ or its tangent. If, at the same time, the arm of potentiometer 46 which is connected to amplifier input 75 were at its midpoint of the resistance, ½ volt would appear on this arm. Now if $\theta$ and, hence, tan $\theta S$ changed so that the arm of potentiometer 48 were at the midpoint of potentiometer 48, ½ volt would appear on the arm and ½ × ½ or ¼ volt would appear on the arm of potentiometer 46, that is, if YI or the height of the intensifier remained the same. Thus, the potential on the arm of potentiometer 46 is always equal to the product of the signal corresponding with the height YI and the signal corresponding with tan $\theta$. Balance of the two input signals is thus obtained when, expressed mathematically, XI = YI tan $\theta$S. Thus, when the potential which is a function of the longitudinal position (XI) of the intensifier, is changed by moving the intensifier, the new potential is applied to one input 76 of comparator servo control 73. This causes motor MS or 66 to drive the arm on which the potential representing tan $\theta$S is developed and drive continues until the potential corresponding with YI tan $\theta$S is developed on the arm of potentiometer 46. Then null is reached and the X-ray source 21 is angulated properly.

If the intensifier height (YI) function potential is changed simultaneously or sequentially with a change in the longitudinal position, of the intensifier, the potential on the arm on potentiometer 46 connected to amplifier input 75 will change. This potential change on input 75 of comparator servo control 73 causes motor 66 or MS to again change the potential on the arm of potentiometer 48 representing tan $\theta$S until null is reached.

It should be noted that whenever the potential on the arm of potentiometer 48 corresponding with tan $\theta$S changes, due to angulating the X-ray source or to raising or lowering the intensifier, the potential to input 77 of the intensifier comparator servo control 72 will change. This results in the intensifier angulating motor 65 or MI running until the potential representing tan $\theta$S is nulled by the potential representing tan $\theta$I in which case the angulations of the X-ray source and intensifier become equal.

It may be desirable to move the X-ray table top automatically to keep the same region of the anatomy in the center of the X-ray beam during the angulation as before angulation of the intensifier. In FIG. 4, assume that a point in the region of interest was initially somewhere around the point marked 81 in FIG. 4. When the intensifier shifted through the distance XI, it would be necessary to shift the point 81 in the anatomy through the distance XT in FIG. 4 so that the X-ray beam 34 would pass through the shifted position of the point 81′ in FIG. 4. Referring to FIG. 3 again, it will be noted that when X-ray source angulating motor 66 or MS was being driven, the potential representing tan $\theta$S on the arm of potentiometer 48 was also applied to an input 79 of servo amplifier 71 as well as to input 77 of amplifier 72 as discussed above. This results in table top motor MT driving the table top to locate 81′ in the X-ray beam. Motor MT drives until the arm on potentiometer 49 which has the potential corresponding with XT on it and is connected to input 80 reaches null. At null, the potential representing tan $\theta$S is proportional to the potential representing XT, which satisfies the geometry of FIG. 4. Now point 81 has been moved proportionately to the change in tan $\theta$S that was initiated by the operator shifting the image intensifier longitudinally. Of course, the system functions in substantially the same way if the intensifier 30 is moved to the right or left as those skilled in the art will realize.

To continue the functional example, assume now that the image intensifier has been shifted longitudinally as described above and it has angulated automatically with the X-ray source 21 so that the central X-ray beam 34 is perpendicular to intensifier's input image plane 33 and centered thereon. Now assume further that the plane of interest in the patient's anatomy still cannot be viewed fluoroscopically to the operator's satisfaction. Under such circumstances lowering or raising image intensifier 30 may be required. If the intensifier 30 is lowered, for example, it will angulate counterclockwise as viewed in FIG. 2 and the source 21 will also angulate similarly to maintain X-ray beam perpendicularity as described heretofore. When the intensifier is lowered, usually manually, meaning that YI has changed an error signal is produced on the arm of potentiometer 46. This signal is applied to input 75 of servo amplifier 73, thus causing motor 66 or MS to operate. This drives the X-ray source 21 through a new angle $\theta$S and the intensifier assumes a corrected angle $\theta$I as described above. Motor MS stops when the error signal due to a change in YI is nulled. When motor MS is running and changing the X-ray source angle $\theta$S, a signal is developed on the arm of potentiometer 48 which results in a change in the signal corresponding with tan $\theta$S. This signal is applied to input 79 of servo amplifier 71 and causes longitudinal table shifting motor MT to operate and shift the patient longitudinally over the distance XT.

To summarize the functional description thus far given, if the operator shifts carriage 40 and the intensifier 30 supported thereon longitudinally along the X-ray table, XI is caused to change, producing an error signal which operates the X-ray tube angulation motor MS, angulating the tube to follow the intensifier. This in turn changes tan $\theta$S, rebalancing that portion of the bridge. However, an error signal is now produced in another portion, causing intensifier angulation motor MI to operate and change the signal corresponding with tan $\theta$I until that error signal vanishes, thus aligning the intensifier and the X-ray tube. If the intensifier is moved vertically, the signal for YI changes, causing the X-ray tube angulation motor to drive the X-ray tube to following the intensifier and rebalance that portion of the bridge. As described above, this unbalances the other portion causing the intensifier to rotate to the same angle as the X-ray tube. In the described embodiment wherein the table top shifts automatically to keep the desired portion of the anatomy in the X-ray beam during angulation, motor 68 or MT is operated concurrently with the intensifier and X-ray source angulation. In other words, whenever the tube angle $\theta$S changes, a third error signal drives the table motor MT or 68 until the error vanishes.

Another feature alluded to above, is the height adjustment of the X-ray tube casing 21 and the table top 10 which must move vertically together. The table and source are raised and lowered jointly with motor 60 which is also marked MST. The motor may be operated with manually responsive control circuitry, not shown.

In reference to FIG. 3, when motor MST 60 is operated, to change the table and source height, it drives the arms marked Y2 of potentiometers or voltage dividers 50 and 57 such as to effectively produce an error signal corresponding with YI relative to the height of the intensifier. The error signal is applied to input 75 of amplifier 73 which causes X-ray source angulating motor MS to operate and produce the coordinate operation of the intensifier angulating motor MI so that the X-ray source and intensifier change their angles 0S and $\theta$I, respectively, synchronously. In FIG. 4, the height of the intensifier relative to a ground plane 85 is marked Y1. The amount by which the X-ray tube focal spot or rotational axis is raised or lowered is marked Y2. The actual height of the intensifier relative to focal spot axis 22 is represented by YI. It will be seen that YI is equal to Y1-Y2. The height of a plane or point which it is desired to maintain at a constant distance from focal spot 22 is marked K. The correct amount of longitudinal table shift is marked XT. XT is always equal to K tan $\theta S$ hence, the correction in XT required by changing the elevation of focal spot 22 by the distance Y2 is reflected in YI, the vertical distance between the center point 74 of the image plane and the focal spot 22. Accordingly, dimension YI changes when the distance Y2 is developed and, as can be seen in FIG. 3, source angulating motor MS responds to the error signal so generated by angulating the X-ray source through the proper angle $\theta S$. The intensifier 30 angulates concurrently to the desired angle for beam perpendicularity as described above.

Figure 5:
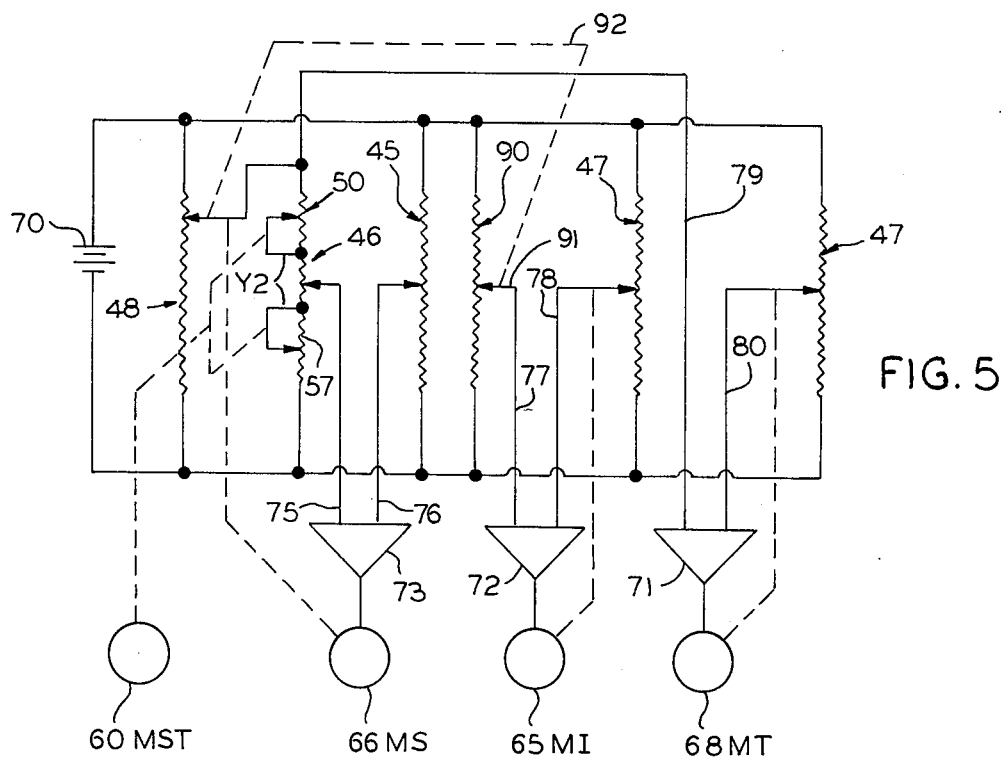
FIG. 5 is a circuit diagram of an alternative embodiment of the invention.
Figure 6:
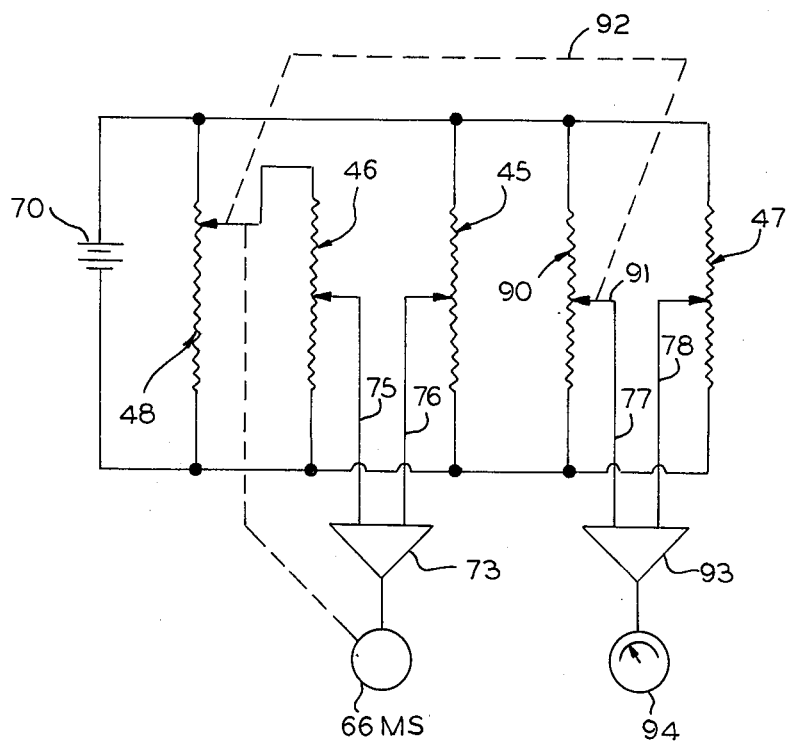
FIG. 6 is a circuit diagram of another alternative embodiment of the invention.

In mathematical terms, the following equations are solved in the bridge circuit of FIGS. 3, 5 and 6: $\theta I = \theta S$; tan $\theta I$ = tan $\theta S$; XI = YI tan $\theta S$; XT = K tan $\theta S$; and, YI = Y1-Y2 where the terms of the equations are the electric signal counterparts of distance and angles.

The intensifier 30 angulation cannot change inadvertently nor can it be changed manually. Any attempt to angulate it by hand would tend to change the potential representing tan $\theta I$ on input 78 of comparator servo control 72 but the established tan $\theta S$ potential on the input 77 would permit an error signal to remain and the motor 65 or MI would drive the intensifier back to its original position.

Those skilled in the art will appreciate that some users might consider it desirable to automate other motions, such as the motion of the intensifier carrying carriage 40. If this is done, the basic bridge circuit of FIG. 3 will remain the same, the only changes being in the connections of the error amplifiers and coupling of the sensors to the drives. In any case, the bridge must compare the product of the height sensors and the tangent of the angle with the carriage position sensor, and the resulting motions, whether automated or manual, required to obtain a null also result in generation of the product. The bridge circuit may also be arranged with tan $\theta I$ interchanged with tan $\theta S$, but the arrangement shown and described above is preferred since an analysis of tracking error during angulation reveals that the arrangement shown produces a lesser error.

An alternative circuit, which accomplishes essentially the same objectives as the FIG. 3 circuit, is shown in FIG. 5. In the previously described FIG. 3 circuit potentiometer 48 was used to produce a signal corresponding with tan $\theta S$ and potentiometer 47 was used to produce a signal corresponding with tan $\theta I$. Any non-linear potentiometer such as one which produces a voltage proportional to a trigonometric function is much more expensive than a linear device. The FIG. 5 circuit reduces the number of non-linear devices which are required.

In FIG. 5, a linear potentiometer 90 has been inserted for producing a signal proportional to $\theta S$ (instead of tan $\theta S$). Potentiometer 90 is mounted on the X-ray source 21 and, although it is not shown in FIG. 2, it may be mounted in that figure to produce a signal proportional to $\theta S$ similar to the manner in which potentiometer 48 is mounted for producing a signal proportional to tan $\theta S$ as the X-ray source 21 angulates. Potentiometer 90 has an arm 91 which is electrically connected to one input 77 of servo amplifier 72 which controls the image receiving means angulating motor 65 (MI). Potentiometer 47 is converted to a linear potentiometer which will now produce a signal proportional to the angle, $\theta I$, of the image intensifier (instead of a signal proportional to the tan of $\theta I$ as in the FIG. 3 circuit).

Having potentiometer 90 in the circuit, the image intensifier angulation indicating device, potentiometer 47, may now be a linear device for producing a signal proportional to $\theta I$ (instead of tan $\theta I$ as in FIG. 3). Since non-linear potentiometer 48 for producing a signal proportional to tan $\theta S$ and linear potentiometer 90 for producing a signal proportional to $\theta S$ have their arms driven jointly when motor 66 or MS angulates X-ray source 21, tan $\theta S$ and $\theta S$ change simultaneously. This is suggested in FIG. 5 by the dashed line 92.

When the image intensifier 30 is shifted longitudinally over the distance XI in reference to the FIG. 5 circuit, the signal from potentiometer 45 will unbalance the inputs to servo amplifier 73, thus causing X-ray source angulating motor 66 to drive. This changes the signal from potentiometer 48 which is proportional to tan $\theta S$ as in the FIG. 3 circuit. But angulation of the source 21 also changes the signal on linear potentiometer arm 91 which signal is proportional to $\theta S$ and is supplied to one input 77 of servo amplifier 72 which controls the image intensifier angulating motor 65 or MI. The unbalance signal from arm 91 causes motor 65 to angulate the image intensifier 30 and also to change the signal from linear device 47 which appears on input 78 of servo amplifier 72. When the signal from potentiometer 47, corresponding with $\theta I$, balances the signal from potentiometer 90, corresponding with $\theta S$, the $\theta S$ equals $\theta I$ and the X-ray source 21 and image intensifier 30 are similarly angulated.

Those skilled in the art will appreciate that the control system herein described for an X-ray cardiovascular examination table can be made with less sophisticated and with the elimination of some features, depending on the needs and desires of the user. For example, the height adjustment of the table and source could be eliminated with sacrifice of operator's comfort. This could eliminate use of motor MST 60 and voltage dividers or potentiometers 50 and 57. In the most rudimentary models all motions may be subject to manual control in place of using motors in which case the error signals may be detected on meters instead of with null amplifiers. The operator may then position the parts manually until the meters indicate no error signal.

FIG. 6 is a circuit diagram for another alternative embodiment of the invention wherein parts which are similar to those used in previously described embodiments are given the same reference numerals.

In this embodiment the motors are eliminated which are used to translate the X-ray table top 10 longitudinally and to angulate the image intensifier 30. Elimination of these motor drives assures that a patient on the table top cannot be driven into collision with a part of the apparatus such as the image intensifier and that the intensifier will not be struck by an intensifier which is angulated under power. In this case, however, the image intensifier 30 is raised and lowered, angulated and shifted longitudinally by manual force but the X-ray source 21 is angulated with a motor 66. The angular error is detected on a null meter 94 and the intensifier is adjusted angularly until the error with the angle of the X-ray source is zero.

The FIG. 6 system is based on the assumption that the operating radiologist knows the angle which intensifier 30 should make to afford the view of the patient's anatomy which is desired. So the radiologist shifts the intensifier 30 longitudinally to the desired position over the patient and later angulates the intensifier as required.

In FIG. 6 the X-ray source angulating motor 66 is controlled by servo amplifier 73 which has inputs 75 and 76. The signal on input 76 is obtained from the arm of potentiometer 45. This signal is proportional to XI, the longitudinal distance of the intensifier rotational axis from being vertically over the axis of the X-ray source. A signal on input 75 is obtained from the arm of potentiometer 46. This signal is proportional to YI, the height of the image intensifier axis or to YI tan $\theta$ if the intensifier is angulated and raised or lowered from its normal position. As in the previously described embodiments, non-linear potentiometer 48 changes its signal corresponding with tan $\theta S$ as the X-ray source angulating motor runs. Thus, if the signal corresponding with XI on linear potentiometer 45 changes due to longitudinal shifting of the intensifier and whether the signal on the arm of potentiometer 46 corresponding with YI, the height of the intensifier, changes or not, the source angulating motor 66 will run until the two input signals to servo amplifier 73 are nulled. This occurs when manual shifting of the intensifier has been stopped. At this time, the intensifier 30 may not yet be manually angulated by the radiologist but the X-ray source is approximately correctly angulated.

The FIG. 6 circuit also has a linear potentiometer 90 whose arm 91 is driven when the X-ray source angulates as described above. Concurrent driving of potentiometer 90 and potentiometer 48 is indicated by the dashed line 92. The signal on arm 91 of potentiometer 90 is proportional to the angle, $\theta S$, of the X-ray source. This signal constitutes one input 77 to a servo amplifier 93 which drives meter 94. Also connected to an input 78 of amplifier 93 is the arm of potentiometer 47. The signal on this arm is proportional to the angle, $\theta I$, of the image intensifier since potentiometer 47 is driven by turning the intensifier manually.

Thus, when the image intensifier 30 is shifted longitudinally the distance XI and the X-ray source angulates, an error signal corresponding to $\theta S$ is applied to amplifier 93 and the error is manifested on meter 94 which no longer reads zero but reads plus or minus zero on its angularly calibrated scale. Now the radiologist angulates the intensifier and changes the signal on the arm of linear potentiometer 47 which signal is proportional to $\theta I$, the angle of the intensifier. This signal is another input to meter amplifier 93. Hence, when the intensifier angle, $\theta I$, is manually induced to equal the source angle, $\theta S$, their corresponding signals will be nulled and meter 94 will be zero again. Now the X-ray source 21 and intensifier 30 are at the same angle and aligned.

Raising or lowering the intensifier will change the signal from potentiometer 46 to unbalance the inputs to amplifier 73 and source angulating motor 66 will run until a new null point is reached. The new angle of the X-ray source results in a meter 94 error which calls for angulating the intensifier manually until the error disappears and $\theta S$ and $\theta I$ become equal again.

Those skilled in the art will recognize that the table top translation motor 68 or MT may be eliminated and that the top may be moved manually and its position could be indicated with a meter, not shown. In such case, if the intensifier is angulated the meter will indicate an error and the table top may be shifted so the X-ray beam will be aimed generally through the same portion of the patient's anatomy.

Although in the above described embodiment potentiometers were used to develop angulation and position error signals, those skilled in the art will appreciate that other more complex means may be used when economically feasible such as digital logic circuitry or other analog circuits. The potentiometer bridge circuit herein described, however, is simple, flexible and reliable and affords an opportunity for illustrating the basic concepts of the invention. Accordingly, although a preferred embodiment has been described in detail, such is intended to be illustrated rather than limiting, for the invention may be variously embodied and is to be limited only by interpretation of the claims which follow.

We claim:

1. X-ray examination apparatus comprising:

X-ray source means and mounting means for mounting said source means for angulating about a first laterally directed axis, first motor means coupled with said source means and operative to effect angulation of said source means in either angular direction about said first axis, another mounting means constructed and arranged for performing longitudinal and vertical movements, X-ray image receiving means mounted on said another mounting means for angulating about a second laterally directed axis, said image receiving means being spaced from said X-ray source means and having an image input plane to which it desired to maintain the X-ray beam from said source means in substantial perpendicularity of all angulations of said source and image receiving means, table means for supporting an examination subject between said X-ray source means and said X-ray image receiving means, second motor means coupled with said image receiving means and operative to effect angulation of said receiving means in either angular direction about said second axis, means for producing a signal corresponding with the longitudinal distance (XI) of said image receiving means second axis from the position of said axis when it is on a vertical line with said X-ray source means first axis, means for producing a signal corresponding with the height (YI) of said second axis relative to said first axis, means for producing a signal corresponding with the tangent of the angle ($\theta S$) between said vertical line and the position to which said second axis of said image receiving means is moved longitudinally, means for multiplying said signals corresponding with (YI) and with (tan $\theta S$) to produce a signal corresponding with (YI) (tan $\theta S$), means for comparing said signals corresponding with (XI) and with (YI) (tan $\theta S$) and for controlling operation of said first motor means in response to a difference between said signals, means responsive to existence of said difference by altering said (tan $\theta S$) signal until said signals corresponding with (XI) and (YI tan $\theta S$) are equal, means for producing a signal corresponding with which is a function of the tangent of ($\theta I$), where $\theta I$ is the angle of said image receiving means relative to a vertical line that is parallel to said vertical line, means for comparing said signals corresponding with tan $\theta$I and tan $\theta$S and for controlling operation of said second motor means in response to a difference between said signals, and means responsive to existence of a difference between said last mentioned signals by altering said signal corresponding with (tan $\theta$I) until said signals corresponding with (tan $\theta$I) and (tan $\theta$S) are equal.

2. The apparatus in claim 1 including:

third motor means coupled with said table means and operative to translate said table means longitudinally in either direction, means for causing said third motor means to translate said table longitudinally in proportion to the longitudinal distance through which said image receiving means second axis is translated so that a point in said examination subject will form said angle ($\theta$S) and be in said X-ray beam after said image receiving means is translated substantially at the same place it was before it was translated, the height of said point above said first axis being represented by (K), the distance for said point to move being represented by (XT), and (XT) divided by (K) being equal to (tan $\theta$S), means for producing a signal which corresponds with (K) (tan $\theta$S), means for comparing the aforesaid signal corresponding with (tan $\theta$S) and the signal corresponding with (K) (tan $\theta$S) and for controlling operation of said third motor means in response to a difference between said signals, and means responsive to existence of said last mentioned difference signal by altering said (K) (tan $\theta$S) signal until said signals corresponding with (tan $\theta$S) and (K) (tan $\theta$S) are equal.

3. The apparatus in claim 2 including:

support means for supporting said table means and said X-ray source means for being moved vertically jointly, fourth motor means coupled with said support means and operative to raise and lower said support means, the height of said image receiving means second axis above a reference level being represented by (Y1) and the height of said source first axis being represented by (Y2) and as aforesaid, the height of said second axis relative to said first axis being represented by (YI) such that (YI) = (Y1) − (Y2), means controlled by said fourth motor means for altering said signal that is a function of said height (YI) of said second axis relative to said first axis until said signal is equal to a signal corresponding with the difference between (Y1) and (Y2).

4. X-ray examination apparatus comprising:

X-ray source means and mounting means for mounting said source means for angulating about a first laterally directed axis, first motor means coupled with said source means and operative to effect angulation of said source means in either angular direction about said first axis, another mounting means constructed and arranged for performing longitudinal and vertical movements, X-ray image receiving means mounted on said another mounting means for angulating about a second axis, said image receiving means being spaced from said X-ray source means, table means for supporting an examination subject between said X-ray source means and said X-ray image receiving means, second motor means coupled with said image receiving means and operative to effect angulation of said receiving means in either angular direction about said second axis, means for producing a signal corresponding with the longitudinal distance (XI) of said image receiving means second axis from the position of said axis when it is on a vertical line with said X-ray source means first axis, means for producing a signal corresponding with the height (YI) of said second axis relative to said first axis, means for producing a signal corresponding with the tangent of the angle ($\theta$S) which is the angle between said vertical line and the position to which said second axis of said image receiving means is moved longitudinally, means for multiplying said signals corresponding with (YI) and (tan $\theta$S) to produce a signal corresponding with (YI) (tan $\theta$S), means for comparing said signals corresponding with (XI) and (YI) (tan $\theta$S) and for controlling operation of said first motor means in response to a difference between said signals, means responsive to existence of said difference by altering said (tan $\theta$S) signal until said signals corresponding with (XI) and (YI tan $\theta$S) are equal, means for producing a signal corresponding with ($\theta$I), the angle of said image receiving means relative to a vertical line that is parallel to said vertical line, means for producing a signal corresponding with the angle $\theta$S, and means for comparing said signals corresponding with the angle $\theta$I and the angle $\theta$S and for controlling operation of said second motor means to run in response to a difference between said signals until said difference is nulled.

5. The apparatus in claim 4 including:

third motor means coupled with said table means and operative to translate said table means longitudinally in either direction, means for causing said third motor means to translate said table longitudinally in proportion to the longitudinal distance through which said image receiving means second axis is translated so that a point in said examination subject will form said angle ($\theta$S) and be in said X-ray beam after said image receiving means is translated substantially at the same place it was before it was translated, the height of said point above said first axis being represented by (K), the distance for said point to move being represented by (XT), and (XT) divided by (K) being equal to (tan $\theta$S), means for producing a signal which corresponds with (K) (tan $\theta$S), means for comparing the aforesaid signal correspondingwith (tan $\theta$S) and the signal corresponding with (K) (tan $\theta$S) and for controlling operation of said third motor means in response to a difference between said signals, and means responsive to existence of said last mentioned difference signal by altering said (K) (tan θS) signal until said signals corresponding with (tan θS) and (K) (tan θS) are equal.

6. The apparatus in claim 5 including:

support means for supporting said table means and said X-ray source means for being moved vertically jointly, fourth motor means coupled with said support means and operative to raise and lower said support means, the height of said image receiving means second axis above a reference level being represented by (Y1) and the height of said source first axis being represented by (Y2) and as aforesaid, the height of said second axis relative to said first axis being represented by (YI) such that (YI) = (Y1) − (Y2), means controlled by said four motor means for altering said signal that is a function of said height (YI) of said second axis relative to said first axis until said signal is equal to a signal corresponding with the difference between (Y1) and (Y2).

7. X-ray examination apparatus comprising:

X-ray source means and means mounting said source means for angulating about a first laterally directed axis, first angulating motor means coupled with said source means and operative to effect angulation of said source means in either angular direction about said first axis, another mounting means constructed and arranged for enabling longitudinal and vertical movements, X-ray image receiving means having an image input plane to which it is desired to maintain the X-ray beam from said source means is substantial perpendicularity, said receiving means being mounted on said another mounting means for angulating about a second laterally directed axis which is not coincident with said first axis, second angulating motor means coupled with said image receiving means and operative to effect angulation of said image receiving means in either angular direction about said second axis, and means for controlling said first and second motor means to angulate said image receiving means and said X-ray source means substantially synchronously in opposite angular directions in response to changes in either and both of the longitudinal and vertical positions of said image receiving means.

8. The apparatus in claim 7 wherein said means for controlling said first and second motor means comprises:

means for producing electric signals representative of the longitudinal and vertical positions of said image receiving means, control means for said first angulating motor means responsive to said signals by angulating said X-ray source means toward said image receiving means, means for producing a signal corresponding with the angle of said source means, and control means for said second angulating motor means responsive to said signal which corresponds with said angle by angulating said receiving means to the same angle as said source means.

9. The apparatus in claim 7 including:

table means for supporting an examination subject between said X-ray source means and image receiving means, third motor means coupled with said table means and operative to translate said table means longitudinally in either direction, means for producing an electric signal corresponding with the longitudinal position of said table means, means for controlling said table translating third motor means to operate and translate said table longitudinally proportionately to the amount by which said one of said source means and said image receiving means is angulated in response to said signal which corresponds with the angulation of said one means so that a region of the subject which is in said beam before said image receiving means is translated longitudinally will be substantially the same region in the beam after said receiving means is translated.

10. The apparatus in claim 8 including:

means for supporting said X-ray source means and said table means for being moved vertically jointly, fourth motor means coupled with said support means and operative to raise and lower said support means and operative to raise and lower said support means, and means responding to the elevation of said support means by altering the said electric signal which corresponds with the vertical position of said image receiving means.

11. X-ray apparatus comprising:

table means for supporting a patient, mounting means that are movable longitudinally and vertically, an X-ray image receiving means mounted on said mounting means for angulating about a laterally directed axis, said device having an X-ray image input plane substantially parallel with its axis, means for mounting an X-ray source on the side opposite of said table means from said receiving device, X-ray source means mounted on said last named mounting means for angulating about a laterally directed axis, motor means operatively coupled with said receiving means for angulating it about its axis, motor means operatively coupled with said X-ray source means for angulating it about its axis, means for producing a first electric signal corresponding with the longitudinal position of said image receiving means and means for producing a second signal corresponding with the vertical position of said means, control means for effecting operation of the X-ray source angulating motor means in response to one and another input signals, control means for effecting operation of the X-ray image receiving means angulating motor in response to one and another input signals, means for producing a third electric signal corresponding with the angle to which one of said X-ray source and said image receiving means is caused to angulate by said first and second electric signals being applied as input signals to one of said control means, said third electric signal being applied to one input of the other of said control means for effecting operation of the other of said motor means, means for producing a fourth electric signal corresponding with the angle to which the other of said X-ray source and said receiving means is angulated, said fourth signal being altered by operation of said another motor means until said fourth signal balances the signal corresponding with the angle of said one of said X-ray source and image receiving means.

12. The apparatus in claim 11 including:

another motor means operatively connected to said table means for translating said table means longitudinally, control means for controlling said table translating motor means in response to one and another input signals one of which is a signal corresponding with the signal that corresponds with the angle of said one of said one and another of said image receiving means and said X-ray source means and the other of which is a signal corresponding with the longitudinal position of said table means, and means for producing said last named signal in response to operation of said another motor means, said signal being altered until it balances said signal corresponding with said angle so that said table will be driven longitudinally in proportion to said angle.

13. The apparatus in claim 12 including:

motor means for selectively raising and lowering said X-ray source and table means jointly, and means responsive to operation of said last named motor means by altering said signal which corresponds with said vertical position of said one of said one and another of said image receiving means and said X-ray source means.

14. The apparatus in claim 12 including:

means for enclosing said X-ray source means.

15. X-ray examination apparatus comprising:

X-ray source means and mounting means for mounting said source means for angulating about a first laterally directed axis, first motor means coupled with said source means and operative to effect angulation of said source means in either angular direction about said first axis, another mounting means constructed and arranged for performing longitudinal and vertical movements, X-ray image receiving means mounted on said another mounting means for angulating about a second laterally directed axis, said image receiving means being spaced from said X-ray source means, table means for supporting an examination subject between said X-ray source means and said X-ray image receiving means, means for producing a signal corresponding with the longitudinal distance (XI) of said image receiving means second axis from the position of said axis when it is on a vertical line with said X-ray source means first axis, means for producing a signal corresponding with the height (YI) of said second axis relative to said first axis, means for producing a signal corresponding with the tangent of the angle ($\theta S$) between said vertical line and the position to which said second axis of said image receiving means is move longitudinally, means for multiplying said signals corresponding with (YI) and (tan $\theta S$) to produce a signal corresponding with (YI) (tan $\theta S$), means for comparing said signals corresponding with (XI) and with (YI) (tan $\theta S$) and for controlling operation of said first motor means to angulate said X-ray source means in response to a difference between said signals, means responsive to existence of said difference by altering said signal corresponding with (tan $\theta S$) until said signals corresponding with (XI) and with (YI tan $\theta S$) are nulled, means for producing a signal corresponding with the angle ($\theta S$) of said X-ray source, means for producing a signal corresponding with the angle ($\theta I$) of said image receiving means, and means for indicating the difference between said signals corresponding with the angles ($\theta S$) and ($\theta I$), to enable said image receiving means to be turned until the difference between said angles ($\theta S$) and ($\theta I$) is reduced to zero.

16. A method of disposing a pivotally mounted X-ray image device and a pivotally mounted X-ray source device at the same angle and in alignment with each other in an arrangement where said devices are spaced apart to enable accommodating an examination subject between them and at least one of said devices is subject to adjustment of its height and longitudinal positions, comprising the steps of:

producing a first signal that is a function of the longitudinal position of said one device, producing a second signal that is a function of the tangent of the angle to which said one device is pivoted and to the height of said other device, producing a third signal that is a function of the angle to which said one device is pivoted, producing a fourth signal that is a function of the angle to which said other device is pivoted, pivoting said one device until the difference between said first and second signals is nulled and said third signal has attained a value corresponding as aforesaid with the angle of said one device, and then pivoting said other device until the said fourth signal which is a function of its angle nulls said third signal which is a function of the angle of said one device.

17. X-ray apparatus for taking X-ray views of a patient at various longitudinal angles, comprising:

X-ray table means for supporting a patient generally horizontally, mounting means above said table means constructed and arranged for enabling horizontal and vertical movements, an X-ray image receiving device supported on said mounting means for angulating longitudinally about a laterallydirected axis and for selectively moving longitudinally and vertically in correspondence with said mounting means, an image receiving device angulating motor coupled with said device and operative to drive it through a range of longitudinal angles, X-ray source means disposed below said table means and means on which said X-ray source is mounted for angulating abouta laterally directed axis synchronously with said image receiving device, said image receiving device having an image input plane generally parallel with its said axis and with which it is desired to keep the central ray from said X-ray source substantially perpendicular for all angulations, source angulating motor means coupled with said X-ray source means and operative to drive it through a range of longitudinal angles, potentiometers which produce signals, respectively, corresponding with the longitudinal and height positions to which said image receiving device is moved, control means for controlling operation of said X-ray source angulating motor, said control means having inputs for said signals and effecting operation of said source angulating motor means when said signals are unbalanced, another potentiometer for producing a signal corresponding with the longitudinal angle of said X-ray source means resulting from signals that correspond with said height and longitudinal positions, said another potentiometer signal being varied in response to operation of said source angulating motor means, control means for controlling operation of said image receiving device angulating motor, said control means having inputs for at least two signals one of which is said signal corresponding with the longitudinal angle of said source means and the other of which is a signal corresponding with the longitudinal angle of said image receiving device, said control means effecting operation of said device angulating motor means when said signals are unbalanced, potentiometer means for producing said signal corresponding with the angle of said device, said last named potentiometer means being varied in response to operation of said device angulating motor means such that said motor means will stop operating when its input signals are in balance whereby said device and source will be at the same longitudinal angle and said central ray will be directed substantially perpendicular to said image input plane.

18. The apparatus in claim 17 including:

motor means operatively coupled with said table means for translating said table means longitudinally, control means for controlling the table translating motor means, said control means having inputs for a signal corresponding with said angle of said source and for a signal corresponding with the longitudinal position of said table means and effecting operation of said motor means when said signals are unbalanced, another potentiometer for producing said signal corresponding with the longitudinal position of said table means, said potentiometer signal being varied in response to operation of said table translating motor means so that when said input signals become balanced said control means will stop operation of said motor means, whereby said table will translate proportionally to said angle.

19. The apparatus in claim 17 including:

motor means for raising and lowering said source and said table means jointly, other potentiometer means in circuit with said potentiometer means whose signal corresponds with the height of said image receiving device, said other potentiometer means being varied by said last named motor means to thereby alter said signal that corresponds with the height of said device.

20. The apparatus in claim 17 including:

means for enclosing said X-ray source means.

21. X-ray apparatus comprising:

X-ray source means and means for mounting said source means for angulating about a first laterally directed axis, first motor means coupled with said source means and operative to effect angulation of said source means in either angular direction about said first axis, another mounting means constructed and arranged for performing longitudinal and vertical movements, X-ray image receiving means mounted on said another mounting means for angulating about a second laterally directed axis, said image receiving means being spaced from said X-ray source means and having an image input plane to which it desired to maintain the X-ray beam from said source means in substantial perpendicularity for all angulations of said source and image receiving means, table means for supporting an examination subject between said X-ray source means and said image receiving means, second motor means coupled with said image receiving means and operative to effect angulation of said receiving means in either angular direction about said second axis, an electric power source, a first potentiometer means supplied from said power source and operative to produce a signal that is a function of the longitudinal distance, (XI), of said second axis from the position of said axis when it is on a vertical line with said first axis, a second potentiometer means having an end connected to said source and another end operative to produce an output signal that is a function of the vertical height, (YI), of said image receiving means second axis relative to said first axis, a third potentiometer supplied from said source and operative to produce a signal that is a function of (tan $\theta S$) where ($\theta S$) is the angle between said vertical line and said second axis, said signal from said third potentiometer being supplied to said other end of said second potentiometer such that said second potentiometer output signal is (YI) (tan $\theta S$), the product of said signals, control means for controlling said first source angulating motor means, said control means having at least two inputs for receiving, respectively, said signals from said first and third potentiometer means and responding to a difference between said signals by operating said first motor means and angulating said X-ray source means, means responsive to operation of said first motor means by altering the signal from said third potentiometer means and thereby altering the signal corresponding with (YI tan $\theta S$), from said second potentiometer means to one input of said control means until said signal balances the input signal corresponding with (YI), from said first potentiometer to thereby stop said first motor means, fourth potentiometer means supplied from said power source for producing a signal which is a function of (tan $\theta I$) where ($\theta I$) is the angulation of said image receiving means, control means for said second motor means which angulates said image receiving means, said control means having at least two inputs for receiving, respectively, said signal from said fourth potentiometer means and said signal from said third potentiometer means and responding to a difference between said signals by operating said second motor means and angulating said image receiving means synchronously with said X-ray source means, and means responsive to operation of said second motor means by altering the signal from said fourth potentiometer means to one input of said last named control means until said signal balances the signal from said third potentiometer means to thereby stop said second motor means when the angles ($\theta S$) and ($\theta I$) are equal.

22. The apparatus in claim 21 including:

third motor means coupled with said table means and operative to translate said table means in either longitudinal direction, means for causing said third motor means to translate said table longitudinally in proportion to the longitudinal distance through which said image receiving means second axis is translated so that a point in said examination subject will form said angle ($\theta S$) and be in the beam from said X-ray source after said image receiving means is translated at substantially the same place it was before translation, the height of said point being represented by (K), the distance for said point to translate being represented by (XT) and (XT) being equal to (tan $\theta S$) multiplied by a constant (K), fifth potentiometer means supplied from said power source and operative to produce a signal which is a function of (K) (tan $\theta S$), another control means for controlling said third translating motor means, said control means having at least two inputs for receiving, respectively, said signal corresponding with (K) (tan $\theta S$) and said signal from said third potentiometer means corresponding with (tan $\theta S$), said control means responding to a difference in said input signals by operating said table translating third motor means to thereby translate said table means, means responsive to operation of said third motor means by altering the signal from said fifth potentiometer means to one input of said another control means until said signal balances the signal from said third potentiometer means to thereby stop said third motor means when said point is at the same angle $\theta S$ as said image receiving means.

23. The apparatus in claim 21 including:

support means for supporting said table means and said X-ray source means jointly vertically, fourth motor means for raising and lowering said support means, the height of said image receiving means second axis being represented by (Y1) and the height of said source first axis being represented by (Y2) and the height of said second axis being represented by (YI) such that a potential functionally related to (YI) equals the difference between potentials functionally related to and represented by (Y1) − (Y2), potential varying means connected with said second potentiometer means for varying the potential thereof in correspondence with (Y1) − (Y2), and means controlled by said fourth motor means for controlling said varying means such that said first motor means will run until said signal from said second potentiometer means rebalances the signal (XI) which is a function of the longitudinal position of said image receiving means.

* * * * *